(12) United States Patent
Endo

(10) Patent No.: US 7,659,533 B2
(45) Date of Patent: Feb. 9, 2010

(54) RADIOGRAPHIC IMAGING CONTROL APPARATUS AND METHOD FOR CONTROLLING THE SAME

(75) Inventor: Yoshiyuki Endo, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/115,988

(22) Filed: May 6, 2008

(65) Prior Publication Data

US 2008/0277605 A1 Nov. 13, 2008

(30) Foreign Application Priority Data

May 8, 2007 (JP) .............................. 2007-123790

(51) Int. Cl.
*G01N 23/083* (2006.01)
(52) U.S. Cl. .................................................. 250/580
(58) Field of Classification Search ............ 250/370.09, 250/580; 378/108
See application file for complete search history.

(56) References Cited

U.S. PATENT DOCUMENTS

| 4,942,596 | A | * | 7/1990 | Eberhard et al. ............ 378/109 |
| 5,485,494 | A | | 1/1996 | Williams et al. |
| 6,208,710 | B1 | * | 3/2001 | Nagai .......................... 378/108 |
| 6,438,201 | B1 | * | 8/2002 | Mazess et al. ................ 378/56 |
| 2004/0202277 | A1 | | 10/2004 | Okumura et al. |
| 2005/0169425 | A1 | * | 8/2005 | Takasawa ..................... 378/97 |

FOREIGN PATENT DOCUMENTS

| JP | 2004-77709 A | 3/2004 |
| JP | 2005-124975 A | 5/2005 |
| WO | WO03/022016 A2 | 3/2003 |

* cited by examiner

*Primary Examiner*—David P Porta
*Assistant Examiner*—Marcus H Taningco
(74) *Attorney, Agent, or Firm*—Canon U.S.A., Inc., IP Division

(57) ABSTRACT

A radiographic imaging control apparatus includes an input unit configured to input a radiographic image from a sensor that detects radiant ray, and a control unit configured to cause a radiant ray generation apparatus to decrease the flux of radiant ray from a predetermined maximum value to a predetermined minimum value as time passes when the radiant ray generation apparatus irradiates the sensor with radiant ray.

10 Claims, 12 Drawing Sheets

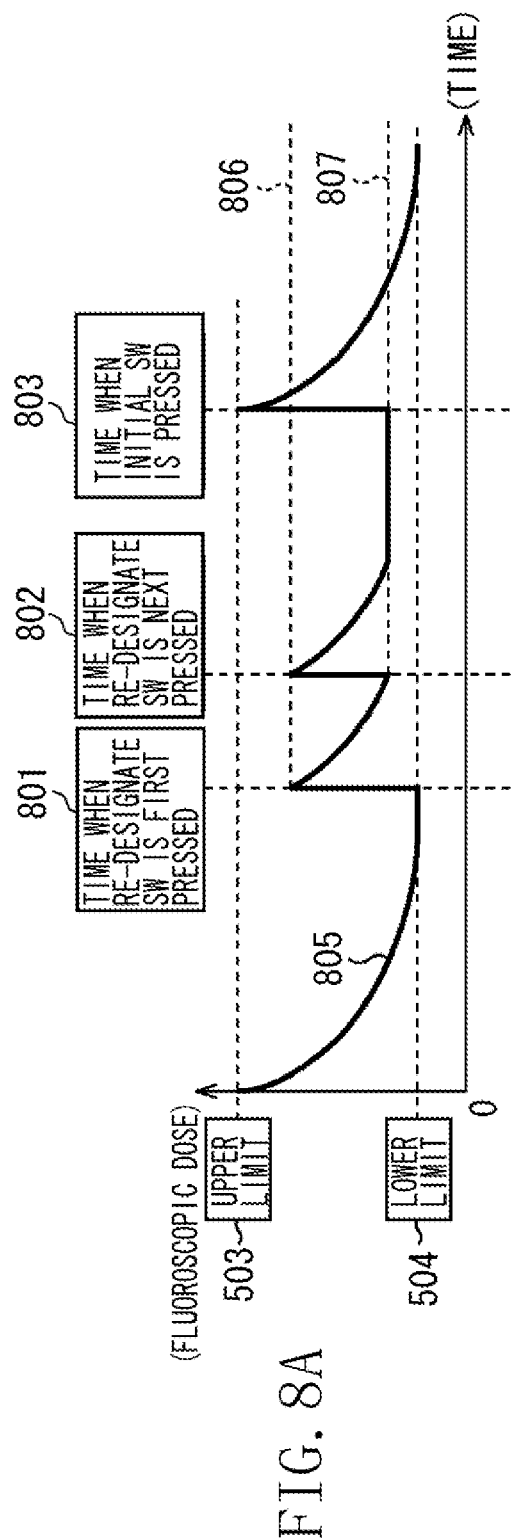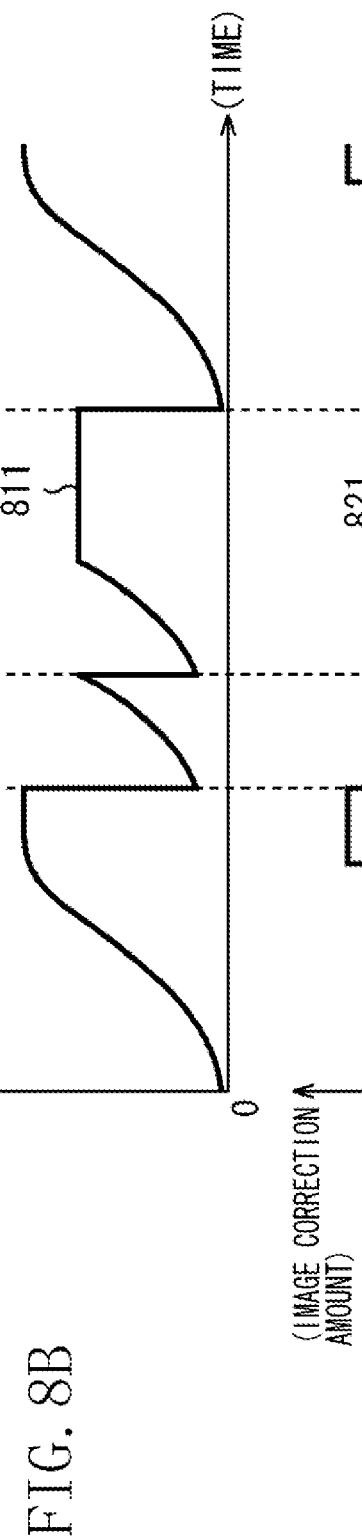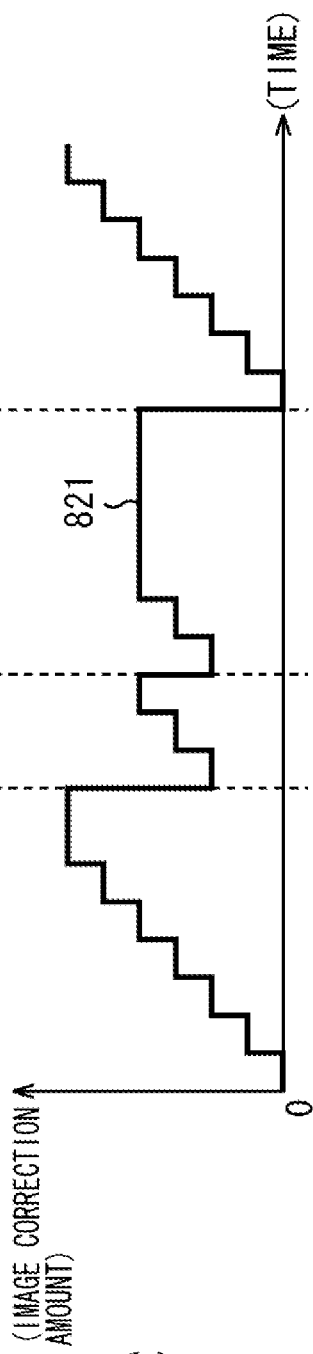

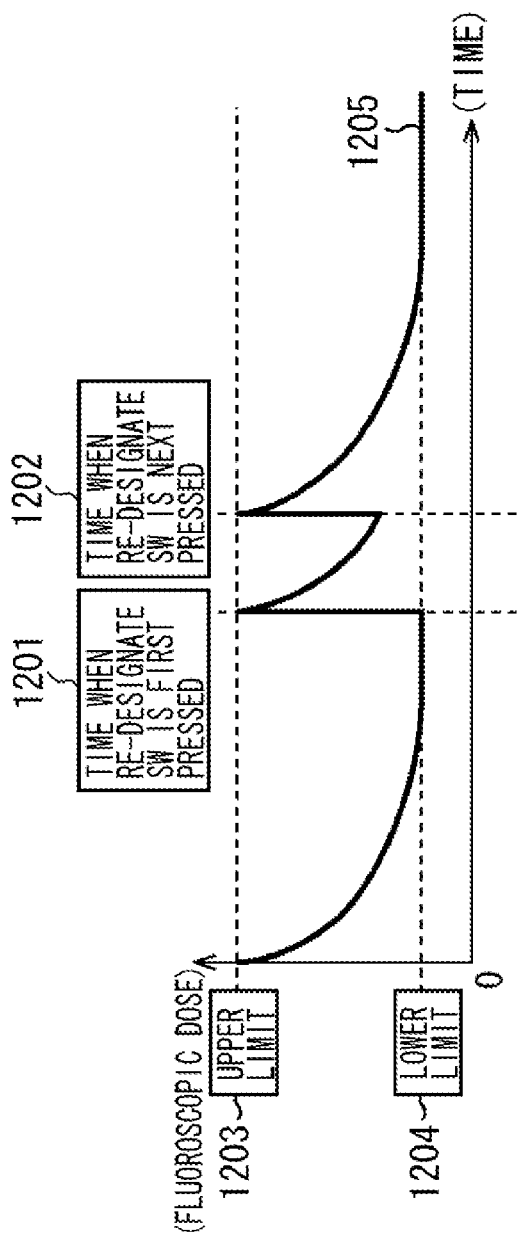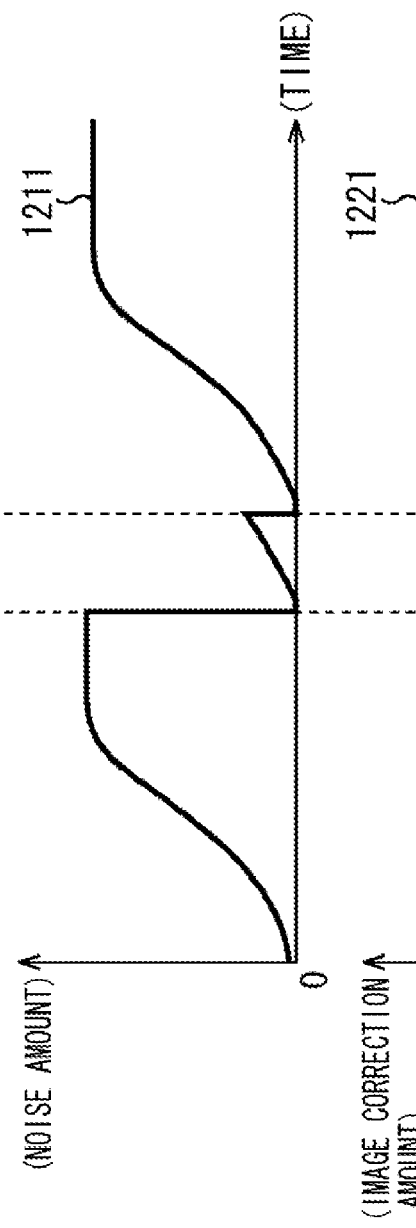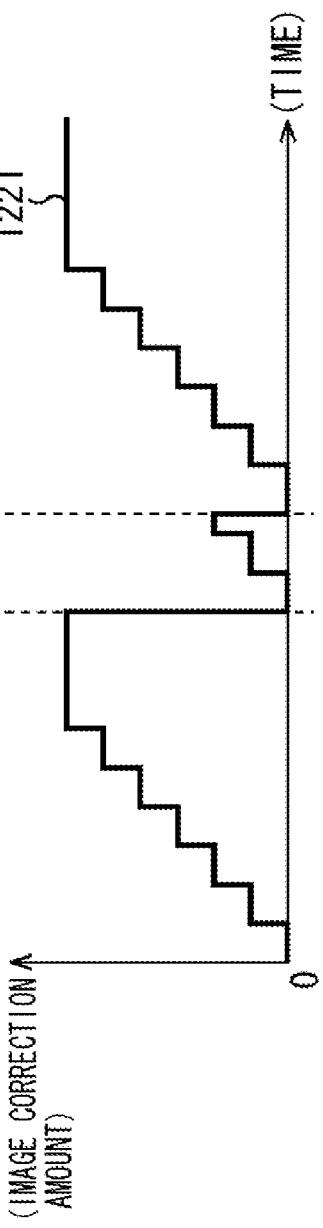

RADIOGRAPHIC IMAGING CONTROL APPARATUS AND METHOD FOR CONTROLLING THE SAME

BACKGROUND OF THE INVENTION

1. Field of the Invention

The present invention relates to a radiographic imaging control apparatus for controlling a radiant ray generation apparatus configured to irradiate a subject with radiant rays.

2. Description of the Related Art

A conventional radiographic imaging system can detect a transmission distribution of radiant rays (represented by X-rays) having been transmitted through a subject, and can be used in a medical field to help diagnose by imaging the inside of a human body.

As discussed in Japanese Patent Application Laid-Open No. 2005-124975, a conventional radiographic imaging system can realize real-time suppression of radiation exposure by changing the level of X-ray dose according to a portion of a human body to be diagnosed.

Furthermore, as discussed in Japanese Patent Application Laid-Open No. 2004-77709, the dose of X-rays used in the diagnosis of a human body can be changed according to a status of a display unit that displays radiographic image information.

However, in the imaging of a human body based on transmission of X-ray, it is inevitable that the human body is significantly exposed to the X-ray. In general, detailed diagnosis of a human body requires a higher level of X-rays and increases the risk of damaging the human body with the X-rays. On the other hand, if the level of X-ray dose is lowered for the purpose of suppressing radiation damage, the image quality of a radiographic image deteriorates due to generation and increase of noise. Thus, the X-ray procedure can cause a problem for medical purposes.

The above-described conventional system is configured to control the X-ray dose to an appropriate level according to the purpose of a radiographic imaging operation. However, according to the above-described conventional system, the X-ray dose is fixed to a predetermined level in an initial state and, after the system starts a radiographic imaging operation, an operator is allowed to manually change the X-ray dose. Therefore, the subject may be unwittingly exposed to a higher level of X-ray for a long time.

Conventional radiographic imaging systems cannot prevent the image quality of a radiographic image from deteriorating without excessively irradiating the subject.

SUMMARY OF THE INVENTION

Exemplary embodiments of the present invention are directed to a radiographic imaging control apparatus capable of preventing the image quality of a radiographic image from deteriorating without excessively irradiating a subject.

According to an aspect of the present invention, a radiographic imaging control apparatus includes an input unit configured to input a radiographic image from a sensor that detects radiant rays, and a control unit configured to cause a radiant ray generation apparatus to decrease the flux of radiant rays from an upper-limit level to a lower-limit level as time passes when the radiant ray generation apparatus irradiates the sensor with radiant rays.

According to another aspect of the present invention, a method for controlling a radiographic imaging control apparatus includes decreasing the flux of radiant rays from an upper-limit level value to a lower-limit level as time passes when a sensor is irradiated with radiant rays, and inputting a radiographic image from the sensor.

According to another aspect of the present invention, a radiant ray imaging apparatus includes a radiant ray generating unit, a radiant ray imaging unit configured to provide an image of at least part of a subject formed by radiant rays, a control unit configured to cause a radiant ray generation apparatus to decrease the flux of radiant rays from an upper-limit level to a lower-limit level as time passes when the radiant ray generation apparatus irradiates the radiant ray imaging unit with radiant rays, an image processing unit configured to process radiant ray images, and a display unit configured to display radiant ray images.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments and features of the invention and, together with the description, serve to explain at least some of the principles of the invention.

FIGS. 8A through 8C illustrate a relationship between fluoroscopic flux, noise amount, and image correction amount according to the second exemplary embodiment of the present invention.

FIGS. 12A through 12C illustrate a relationship between fluoroscopic flux, noise amount, and image correction amount according to the second exemplary embodiment of the present invention.

DETAILED DESCRIPTION OF THE EMBODIMENTS

Figure 1:
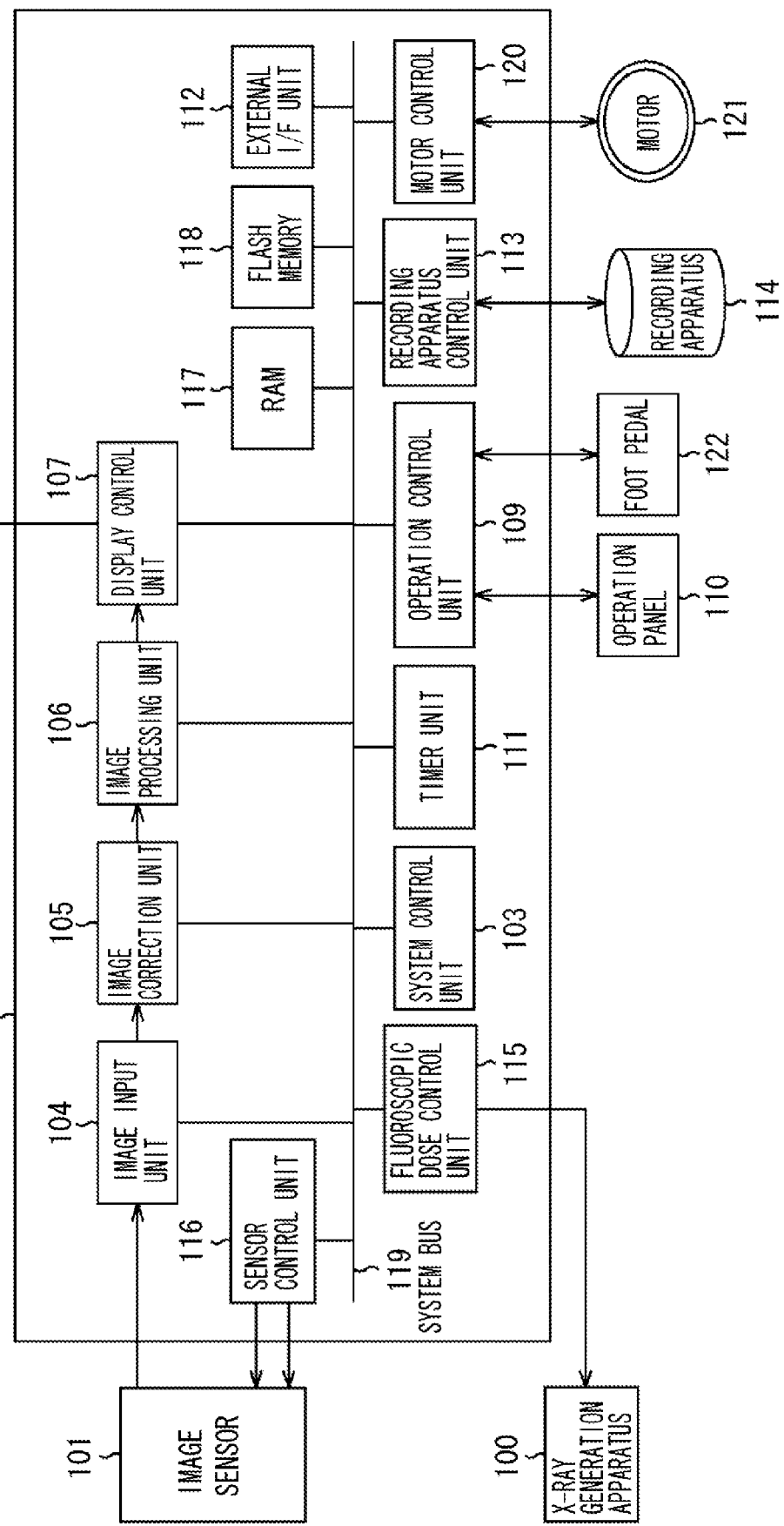
FIG. 1 is a block diagram illustrating an X-ray imaging control apparatus (radiographic imaging control apparatus) according to a first exemplary embodiment of the present invention.

The following description of exemplary embodiments is illustrative in nature and is in no way intended to limit the invention, its application, or uses. Processes, techniques, apparatus, and systems as known by one of ordinary skill in the art are intended to be part of the enabling description where appropriate. It is noted that throughout the specification, similar reference numerals and letters refer to similar items in the following figures, and thus once an item is described in one figure, it may not be discussed for following figures. Exemplary embodiments will be described in detail with reference to the drawings. The radiant rays used in the following exemplary embodiments of the present invention are X-rays. However, other radiant rays (electromagnetic wave represented by visible light, $\alpha$-rays, $\beta$-rays, $\gamma$-rays, etc.) can be also used in the present invention.

First Exemplary Embodiment

A first exemplary embodiment of the present invention is now described with reference to FIGS. 1 through 6. FIG. 1 is a block diagram illustrating an X-ray imaging control apparatus (radiographic imaging control apparatus) according to the first exemplary embodiment of the present invention.

The X-ray imaging control apparatus illustrated in FIG. 1 includes an X-ray generation apparatus (radiant ray generation apparatus) 100, an image sensor 101, an X-ray image processing apparatus (radiographic image processing apparatus or radiation dose control apparatus) 102, a display device 108, an operation panel 110, a recording apparatus 114, a motor 121, and a foot pedal 122.

The X-ray generation apparatus 100 is configured to control the X-ray flux (radiation flux) of X-rays used to irradiate the subject according to a drive voltage supplied from a fluoroscopic flux control unit 115 of the X-ray image processing apparatus 102, to obtain a fluoroscopic image (an X-ray moving image) of the subject. In the following description, the X-ray flux (radiation flux) of X-rays used to irradiate the subject is referred to as the "fluoroscopic flux."

The image sensor 101 detects the intensity distribution (X-ray image) of the X-rays having been transmitted through the subject, and converts it into an electric signal to obtain an X-ray image (radiographic image), i.e., fluoroscopic image, of the subject.

A system control unit 103 of the X-ray image processing apparatus 102 controls various operations performed by the X-ray image processing apparatus 102. The system control unit 103 includes a central processing unit (CPU). For example, the system control unit 103 determines the content of operational information when an operator operates the operation panel 110 or the foot pedal 122. Furthermore, the system control unit 103 performs processing for recording a change in amount of the X-ray flux (fluoroscopic flux).

An image input unit 104 of the X-ray image processing apparatus 102 receives an X-ray image if the X-ray image is input from the image sensor 101 into the X-ray image processing apparatus 102. The image input unit 104 includes an analog-to-digital (A/D) converter that converts an analog signal received from the image sensor 101 (i.e., a signal relating to the X-ray image) into a digital signal.

An image correction unit 105 of the X-ray image processing apparatus 102 performs predetermined image correction processing on the X-ray image input from the image sensor 101 via the image input unit 104. The image correction processing performed by the image correction unit 105 includes noise reduction processing and contour enhancement processing which are performed in a stepwise fashion.

The image correction unit 105 performs image correction processing on an X-ray image obtained when the X-ray generation apparatus 100 irradiates the subject with X-rays. The X-ray image processed by the image correction unit 105 can be output to an image processing unit 106 under the control of the system control unit 103, or can be stored into the recording apparatus 114 via a system bus 119 or output to an external device via an external interface (I/F) unit 112.

The image processing unit 106 of the X-ray image processing apparatus 102 performs predetermined image processing on an input X-ray image. The image processing performed by the image processing unit 106 includes diagnosis-oriented image processing and coding processing. The image processing unit 106 generates image data of a display image to be output to the display device 108. The X-ray image processed by the image processing unit 106 can be stored into the recording apparatus 114 via the system bus 119 under the control of the system control unit 103, or output to an external device via the external I/F unit 112. The display device 108 can display the X-ray image generated by the image processing unit 106.

A display control unit 107 of the X-ray image processing apparatus 102 converts the image data of a display image generated by the image processing unit 106 into image data that the display device 108 can display. The display control unit 107 performs control for causing the display device 108 to display an image based on the image data.

The display device 108 displays an image based on image data of the display image output from the display control unit 107. The display device 108 is, for example, a monitor using a cathode ray tube or a liquid crystal display. For example, an operator operates the operation panel 110 while viewing an X-ray image (fluoroscopic image) displayed on the display device 108.

An operation control unit 109 of the X-ray image processing apparatus 102 receives operational information input from an operator via the operation panel 110 or the foot pedal 122 and performs control for sending the input operational information to the system control unit 103. Furthermore, the operation control unit 109 performs control for displaying the operation status of the X-ray imaging control apparatus on a display part of the operation panel 110.

The operation panel 110 enables an operator to perform various operations such as inputting data while viewing the display panel. The foot pedal 122 enables an operator to perform an ON/OFF control for the X-ray generation apparatus 100 that irradiates a subject with X-rays.

A timer unit 111 of the X-ray image processing apparatus 102 measures elapsed time based on a control signal from the system control unit 103.

The external I/F unit 112 of the X-ray image processing apparatus 102 is an interface that enables the X-ray image processing apparatus 102 to communicate with an external PC or an external apparatus (e.g., diagnosis apparatus). For example, the external I/F unit 112 is Ethernet or USB2.0 network interface.

A recording apparatus control unit 113 of the X-ray image processing apparatus 102 controls the recording apparatus 114.

The recording apparatus 114 is an external storage apparatus which can be optionally and detachably connected to the X-ray image processing apparatus 102. The recording apparatus 114 is, for example, a hard disk, a memory card, a flexible disk (FD), a compact disk (CD), a magnetic card, an optical card, an IC card, or a memory card.

The fluoroscopic flux control unit 115 of the X-ray image processing apparatus 102 controls the flux of X-rays (fluoroscopic flux) when the X-ray generation apparatus 100 irradiates the subject with X-rays and changes the flux of X-rays.

A sensor control unit 116 of the X-ray image processing apparatus 102 outputs a drive timing signal and signals relating to various setting data to the image sensor 101 and controls the operation of the image sensor 101.

A random access memory (RAM) 117 of the X-ray image processing apparatus 102 is a memory configured to temporarily store program(s) and data supplied from an external apparatus or a flash memory 118. The flash memory 118 of the X-ray image processing apparatus 102 is a memory configured to store program(s) and parameters which are not changed.

The system bus 119 of the X-ray image processing apparatus 102 enables each component to transmit and receive data and signal(s) to and from other component in the X-ray image processing apparatus 102.

A motor control unit 120 of the X-ray image processing apparatus 102 controls the operation of each motor 121 provided in the X-ray imaging control apparatus.

The motor 121 is, for example, a driving motor of a bed supporting the subject.

Figure 2:
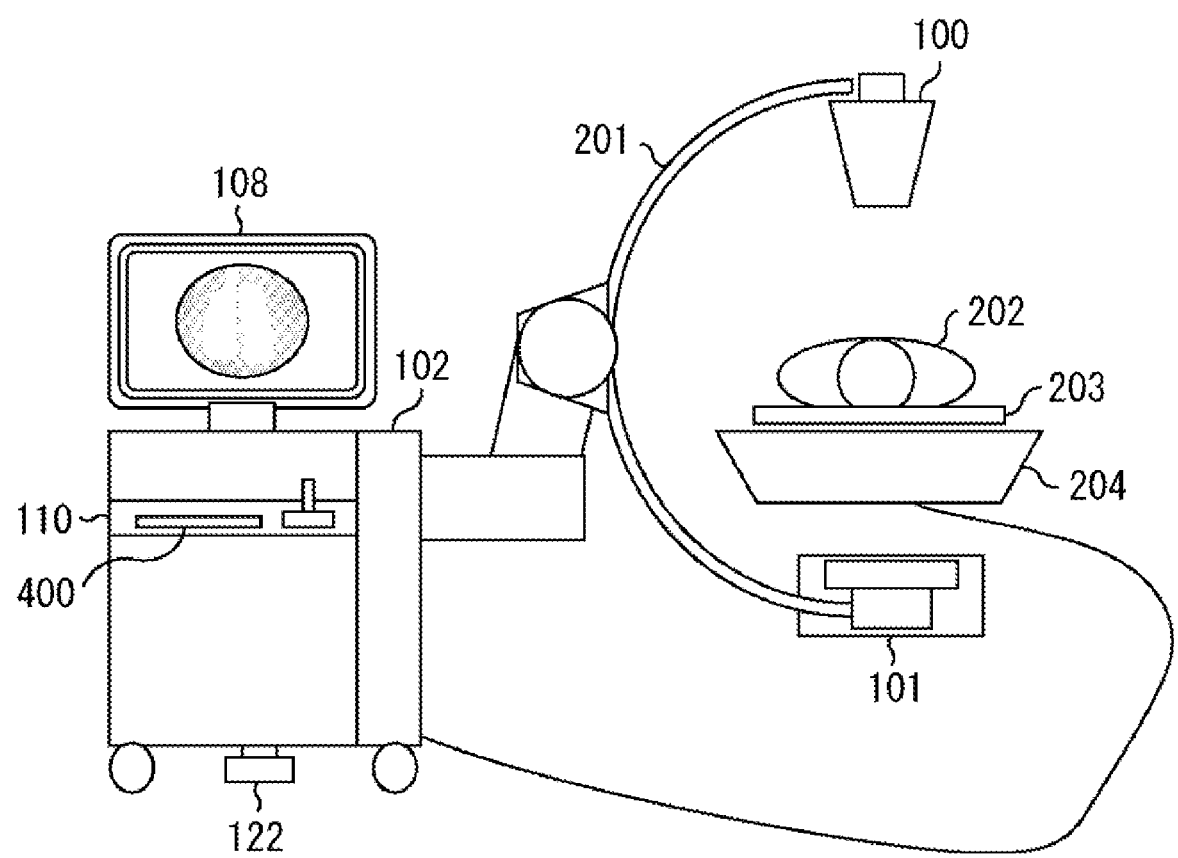
FIG. 2 illustrates a diagnosis system using the X-ray imaging control apparatus (radiographic imaging control apparatus) according to the first exemplary embodiment of the present invention.

FIG. 2 illustrates a system using the X-ray imaging control apparatus (radiographic imaging control apparatus) according to the first exemplary embodiment of the present invention. In FIG. 2, components similar to those illustrated in FIG. 1 are denoted by the same reference numerals.

The diagnosis system illustrated in FIG. 2 includes a C-shaped arm 201 having one end (upper end) supporting the X-ray generation apparatus 100 and the other end (lower end) supporting the image sensor 101 in an opposed or facing relationship. A subject 202 (human body), when mounted on a bed 203, can be positioned on a straight line connecting the X-ray generation apparatus 100 and the image sensor 101. A bed moving apparatus 204 includes a built-in motor 121 that can slide the bed 203 along a predetermined plane. Furthermore, although not illustrated in FIG. 2, the diagnosis system includes a motor 121 attached to the C-shaped arm 201 and configured to drive the C-shaped arm 201.

The operation panel 110 illustrated in FIG. 2 enables an operator to input instructions to drive the C-shaped arm 201 and the bed 203. Furthermore, the operation panel 110 includes an X-ray control operation panel 400 that enables an operator to adjust the flux of X-rays when the X-ray generation apparatus 100 irradiates a subject with X-rays.

Figure 3:
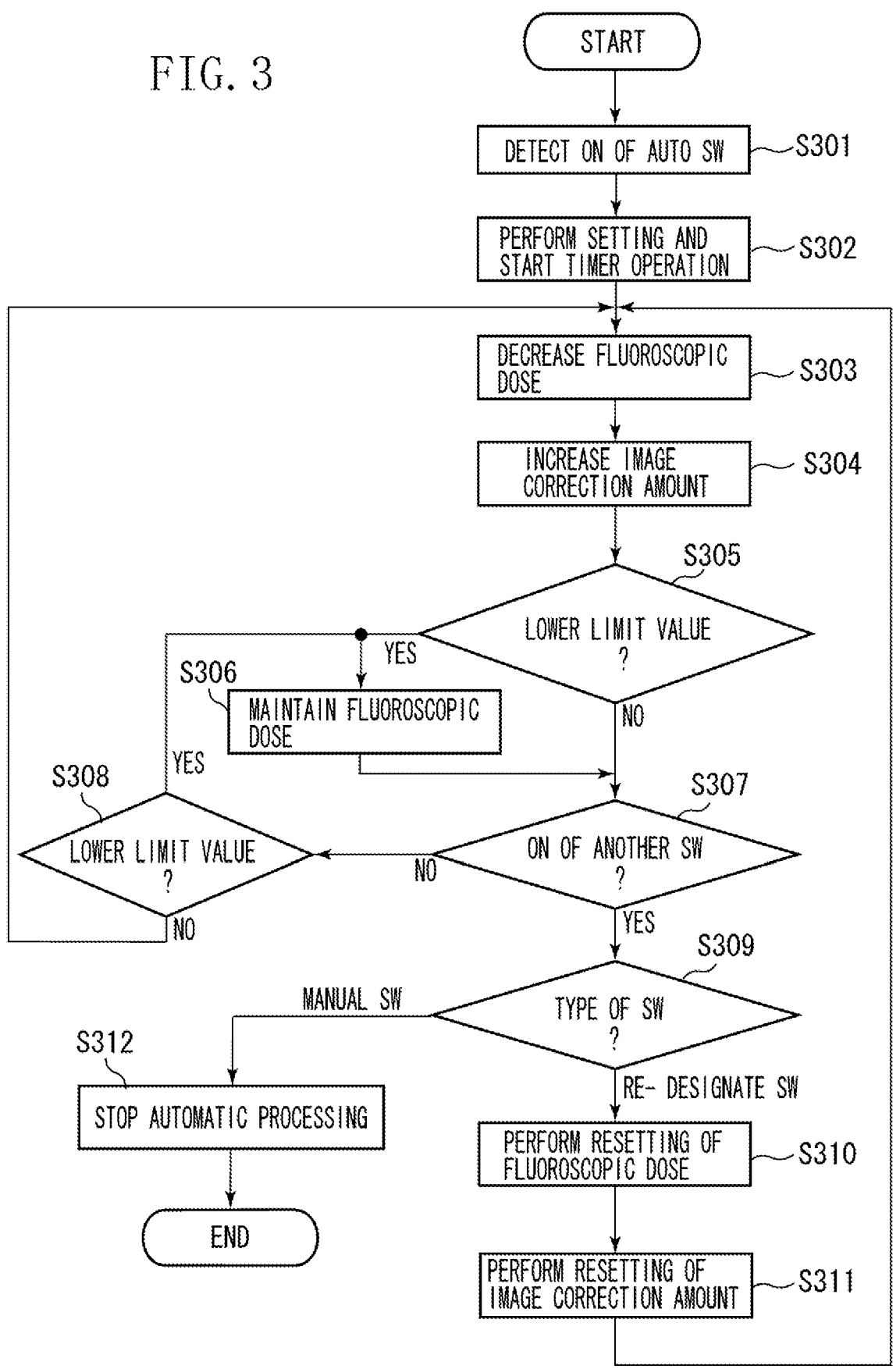
FIG. 3 is a flowchart illustrating processing performed by the X-ray image processing apparatus (radiographic image processing apparatus) according to the first exemplary embodiment of the present invention.

FIG. 3 is a flowchart illustrating processing performed by the X-ray image processing apparatus (radiographic image processing apparatus) 102 according to the first exemplary embodiment of the present invention. The processing (operations) according to this flowchart is described later.

Figure 4:
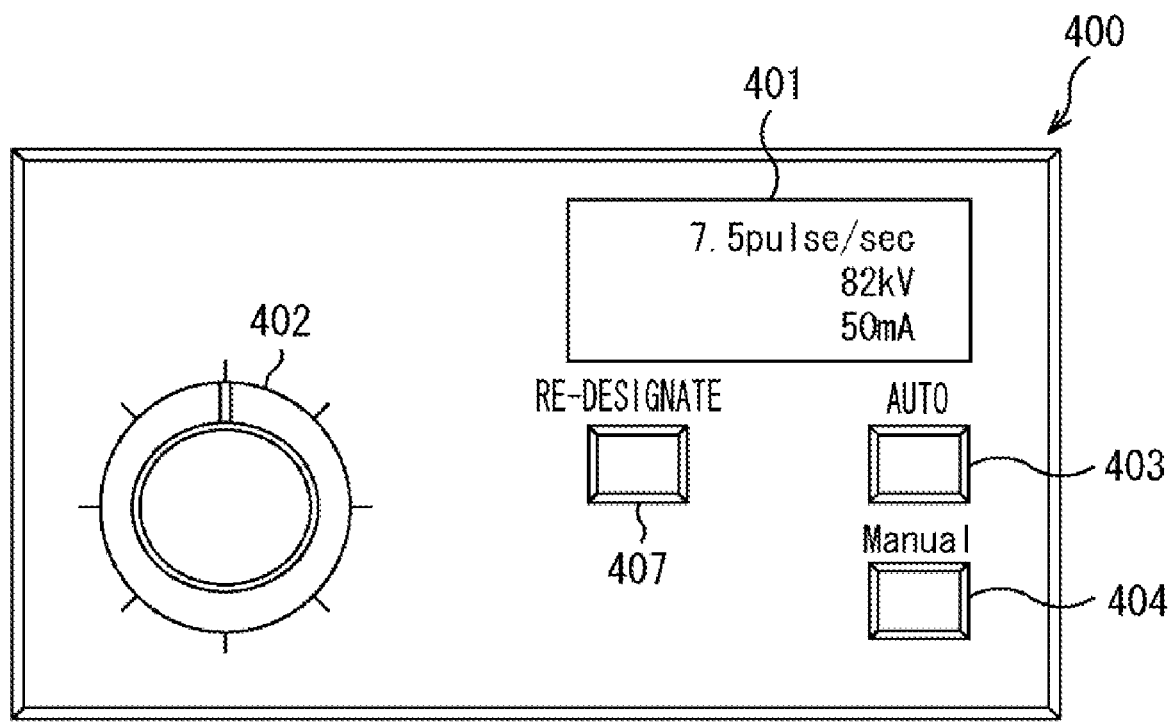
FIG. 4 illustrates an X-ray control operation panel according to the first exemplary embodiment of the present invention.
Figure 5:
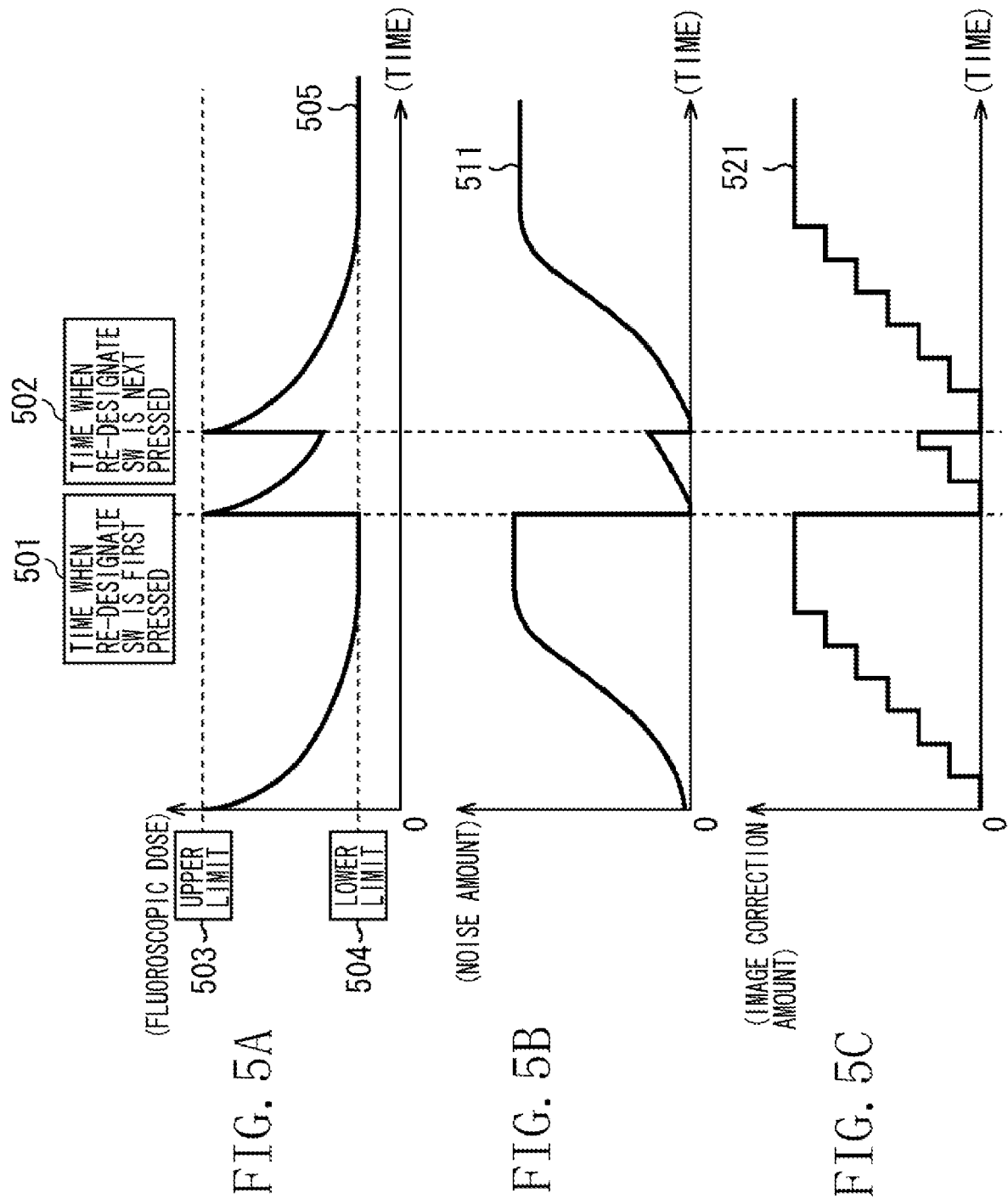
FIGS. 5A through 5C illustrate a relationship between fluoroscopic flux, noise amount, and image correction amount according to the first exemplary embodiment of the present invention.

FIG. 4 illustrates the X-ray control operation panel 400 (FIG. 2) according to the first exemplary embodiment of the present invention. The X-ray control operation panel 400 illustrated in FIG. 4 includes a display panel 401, a potentiometer 402, an automatic switch (AUTO SW) 403, a manual switch (MANUAL SW) 404, and a re-designation switch (RE-DESIGNATE SW) 407.

The display panel 401 displays X-ray related information of the X-ray generation apparatus 100 and also can display an operational state of the system. The potentiometer 402 is an operation unit that enables an operator to change the fluoroscopic flux (the flux of X-rays emitted from the X-ray generation apparatus 100). The AUTO SW 403 enables an operator to select an automatic control of the fluoroscopic flux (the flux of X-ray emitted from the X-ray generation apparatus 100). The MANUAL SW 404 enables an operator to select a manual control of the fluoroscopic flux using the potentiometer 402. The RE-DESIGNATE SW 407 is an operation unit that enables an operator to restore the fluoroscopic flux (the flux of X-rays emitted from the X-ray generation apparatus 100) to a predetermined level (predetermined value).

FIGS. 5A through 5C illustrate a relationship between fluoroscopic flux, noise amount, and image correction amount according to the first exemplary embodiment of the present invention. In FIGS. 5A through 5C, time 501 represents the time when the RE-DESIGNATE SW 407 is first pressed. Furthermore, time 502 represents the time when the RE-DESIGNATE SW 407 is next pressed.

FIG. 5A illustrates the temporal change of the fluoroscopic flux 505 controlled by the system control unit 103 via the fluoroscopic flux control unit 115. If an operator presses the RE-DESIGNATE SW 407, the fluoroscopic flux 505 is restored to a predetermined upper-limit level (maximum value) 503 as illustrated in FIG. 5A. More specifically, the operator presses the RE-DESIGNATE SW 407 at the first time 501 after the fluoroscopic flux 505 has once reached a predetermined lower-limit level (minimum value) 504. Then, the operator presses the RE-DESIGNATE SW 407 again at the second time 502 before the fluoroscopic flux 505 reaches the lower-limit level (minimum value) 504. At each time, the fluoroscopic flux 505 is restored to the predetermined upper-limit level (maximum value) 503 when the operator presses the RE-DESIGNATE SW 407.

In this example, the upper-limit level (maximum value) 503 and the lower-limit level (minimum value) 504 of the fluoroscopic flux 505 illustrated in FIG. 5A can be determined considering a portion of the subject 202 to be imaged. For example, the system control unit 103 performs setting of the upper-limit level (maximum value) 503 and the lower-limit level (minimum value) 504 based on operational information input by an operator via the operation panel 110. Furthermore, after completing the setting processing, the system control unit 103 performs recording (storage) of the upper-limit level (maximum value) 503 and the lower-limit level (minimum value) 504 into predetermined area(s) in the flash memory 118 (i.e., recording medium) which can be managed by the system control unit 103.

FIG. 5B illustrates the temporal change of a noise amount 511 involved in an analog signal of the fluoroscopic image (X-ray image) output from the image sensor 101 according to the change of the fluoroscopic flux 505. As apparent from FIG. 5B, the noise amount 511 increases monotonically according to reduction of the fluoroscopic flux 505 illustrated in FIG. 5A.

FIG. 5C illustrates the temporal change of an image correction amount 521 for the image correction processing performed by the image correction unit 105 under the control of the system control unit 103 to decrease the noise amount 511 generated according to the change of the fluoroscopic flux 505.

As illustrated in FIG. 5C, at the time 501 when the RE-DESIGNATE SW 407 is first pressed, the image correction unit 105 performs processing for restoring the image correction amount to the lowest level in response to the jump of the fluoroscopic flux 505 to the upper-limit level (maximum value) 503. Similarly, at the time 502 when the RE-DESIG- NATE SW 407 is next pressed, the image correction unit 105 performs processing for restoring the image correction amount to the lowest level in response to the jump of the fluoroscopic flux 505 to the upper-limit level (maximum value) 503 even if the image correction amount has an intermediate value. Namely, if an operator presses the RE-DESIGNATE SW 407, the system control unit 103 causes the image correction unit 105 to perform a control for decreasing the image correction amount in response to the jump of the fluoroscopic flux 505 to the upper-limit level (maximum value) 503.

The above-described sequential processing illustrated in FIGS. 5A through 5C can be realized by the system control unit 103 that controls setting values of the fluoroscopic flux control unit 115 and the image correction unit 105 according to time information of the timer unit 111 and an operator's instruction input via the operation panel 110. The flash memory 118 can store, in a predetermined area, a basic change amount applicable to the change amount of the fluoroscopic flux 505 illustrated in FIG. 5A. Furthermore, the flash memory 118 can store, in a predetermined area, a basic correction amount applicable to the image correction amount of the image correction unit 105 corresponding to the change of the fluoroscopic flux 505.

Figure 6:
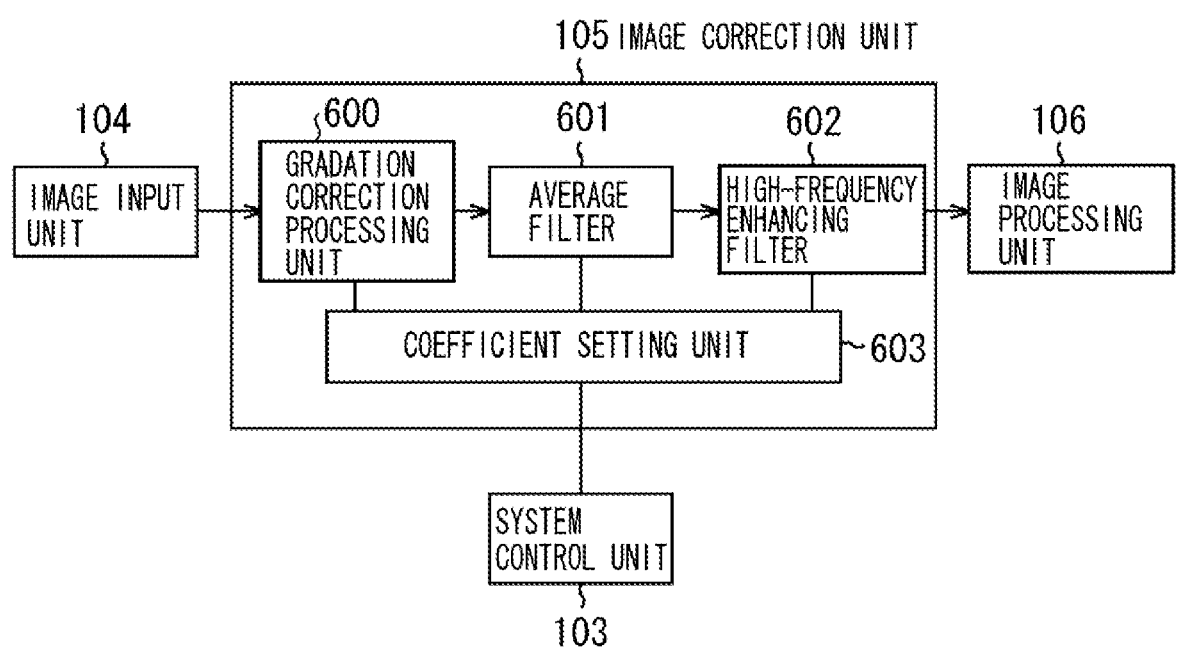
FIG. 6 is a block diagram illustrating a detailed arrangement of an image correction unit in the X-ray image processing apparatus (radiographic image processing apparatus) according to the first exemplary embodiment of the present invention.

FIG. 6 is a block diagram illustrating a detailed arrangement of the image correction unit 105 in the X-ray image processing apparatus (radiographic image processing apparatus) 102 according to the first exemplary embodiment of the present invention.

As illustrated in FIG. 6, the image correction unit 105 includes a gradation correction processing unit 600, an average filter 601, a high-frequency emphasis filter 602, and a coefficient setting unit 603.

The gradation correction processing unit 600 performs gradation correction processing including dodging process correction for correcting the luminance level of an X-ray image (fluoroscopic image) input from the image input unit 104. The average filter 601 is a filter capable of removing noise. The high-frequency emphasis filter 602 is a filter capable of emphasis high-frequency components of an X-ray image processed by the average filter 601 if the image has a vague contour. Namely, the high-frequency emphasis filter 602 can sharpen the contour of an input X-ray image. The coefficient setting unit 603 sets correction coefficients supplied to the gradation correction processing unit 600, the average filter 601, and the high-frequency emphasis filter 602 to adequately adjust their processing mounts.

More specifically, the coefficient setting unit 603 performs setting of coefficients for the gradation correction processing unit 600, the average filter 601 and the high-frequency emphasis filter 602 according to an image correction amount instructed from the system control unit 103 via the system bus 119.

For example, the coefficient setting unit 603 performs the following processing for setting the coefficients. If the image correction amount is small, the coefficient setting unit 603 sets appropriate coefficients in such a manner that the gradation correction processing unit 600 can decrease the luminance adjustment amount to suppress luminance increase at a dark portion, the average filter 601 can decrease the processing amount to reduce the noise removal amount, and the high-frequency emphasis filter 602 can decrease the processing amount.

Furthermore, if the image correction amount is large, the coefficient setting unit 603 sets appropriate coefficients in such a manner that the gradation correction processing unit 600 can increase the luminance adjustment amount to increase the luminance at a dark portion, the average filter 601 can increase the processing amount to increase the noise removal amount, and the high-frequency emphasis filter 602 can increase the processing amount.

The noise removal arrangement illustrated in FIG. 6 is a mere example. According to another exemplary embodiment, the image correction unit 105 can be configured to include a median filter. The high-frequency emphasis filter 602 can be replaced with a contour enhancement filter.

Next, example processing (operations) performed by the X-ray image processing apparatus (radiographic image processing apparatus) 102 according to the first exemplary embodiment of the present invention is described with reference to a flowchart illustrated in FIG. 3.

In step S301, the system control unit 103 detects if the AUTO SW 403 has been switched on via the operation control unit 109 if an operator presses the AUTO SW 403 when the operator performs diagnosis while viewing the display device 108.

In step S302, the system control unit 103 reads setting values relating to the fluoroscopic flux 505 (e.g., upper-limit level (maximum value) 503, lower-limit level (minimum value) 504, and change amount) from a predetermined area of the flash memory 118, and sets the read setting values to the fluoroscopic flux control unit 115. Furthermore, the system control unit 103 reads a setting value relating to the image correction amount 521 from a predetermined area of the flash memory 118, and sets the read setting values to the image correction unit 105. Furthermore, the system control unit 103 causes the timer unit 111 to start a timer operation.

In step S303, the system control unit 103 causes the fluoroscopic flux control unit 115 to decrease the fluoroscopic flux according to the basic change amount represented by the fluoroscopic flux 505 illustrated in FIG. 5A in association with the timer operation of the timer unit 111. The fluoroscopic flux control unit 115 instructs the X-ray generation apparatus 100 to gradually decrease the X-ray flux (fluoroscopic flux) from the predetermined upper-limit level (maximum value) 503 when the X-ray generation apparatus 100 irradiates the subject 202 with X-rays. This control brings preferred effects because human eyes are gradually acclimatized to an image having insufficient image quality with elapsed time.

In step S304, the system control unit 103 causes the image correction unit 105 to perform image correction processing according to the basic setting amount (rate) to decrease the fluoroscopic flux. The image correction unit 105 performs image correction processing based on the image correction amount 521 which increases in a stepwise fashion as illustrated in FIG. 5C. Namely, the system control unit 103 performs control for increasing the image correction amount relating to the image correction processing performed by the image correction unit 105 according to a change amount corresponding to the reduction in the fluoroscopic flux.

In step S305, the system control unit 103 determines whether the fluoroscopic flux 505 has reached the predetermined lower-limit level (minimum value) 504, while constantly monitoring the fluoroscopic flux 505 during the fluoroscopic flux reduction processing having been started in step S303.

If the system control unit 103 determines that the fluoroscopic flux 505 has reached the predetermined lower-limit level (minimum value) 504 (YES in step S305), the processing proceeds to step S306.

In step S306, the system control unit 103 causes the fluoroscopic flux control unit 115 to maintain the fluoroscopic flux 505 at the lower-limit level (minimum value) 504 and also causes the image correction unit 105 to maintain the image correction amount 521 at a present level.

After completing the processing of step S306, the processing proceeds to step S307. Furthermore, if the system control unit 103 determines that the fluoroscopic flux 505 has not yet reached the predetermined lower-limit level (minimum value) 504 (NO in step S305), the processing proceeds to step S307.

In step S307, the system control unit 103 determines whether an operator operates (presses) any switch other than the AUTO SW 403 on the X-ray control operation panel 400 illustrated in FIG. 4. If the system control unit 103 determines that a switch other than the AUTO SW 403 is not operated (pressed) (NO in step S307), the processing proceeds to step S308.

In step S308, the system control unit 103 determines whether the fluoroscopic flux 505 has reached the predetermined lower-limit level (minimum value) 504. If in step S308 it is determined that the fluoroscopic flux 505 has reached the predetermined lower-limit level (minimum value) 504 (YES in step S308), the processing returns to step S306. Furthermore, if the system control unit 103 determines that the fluoroscopic flux 505 has not yet reached the predetermined lower-limit level (minimum value) 504 (NO in step S308), the processing returns to step S303.

If the system control unit 103 determines that a switch other than the AUTO SW 403 is operated (pressed) (YES in step S307), the processing proceeds to step S309.

In step S309, the system control unit 103 identifies the type of switch which the operator has operated (pressed) on the X-ray control operation panel 400. If in step S309 the system control unit 103 determines that the RE-DESIGNATE SW 407 is operated (pressed) by the operator, the processing proceeds to step S310.

In step S310, the system control unit 103 causes the fluoroscopic flux control unit 115 to perform resetting for restoring the fluoroscopic flux 505 to the upper-limit level (maximum value) 503. The fluoroscopic flux control unit 115 instructs the X-ray generation apparatus 100 to restore the X-ray flux (fluoroscopic flux) to the upper-limit level (maximum value) 503 when the X-ray generation apparatus 100 irradiates the subject 202 with X-ray.

In step S311, the system control unit 103 causes the image correction unit 105 to perform processing for restoring the image correction amount 521 (FIG. 5C) to an initial setting value according to the control for restoring the fluoroscopic flux 505 to the upper-limit level (maximum value) 503. The image correction unit 105 performs the image processing with the image correction amount fixed at the lowest level as illustrated in FIG. 5C. After completing the processing of step S311, the processing returns to step S303.

If in step S309 the system control unit 103 determines that the MANUAL SW 404 is operated (pressed) by the operator, the processing proceeds to step S312.

In step S312, the system control unit 103 stops automatic control processing having been performed after the operator has pressed the AUTO SW 403 and enables the operator to start a manual operation based on the processing parameters currently held. Then, the system control unit 103 terminates the processing routine according to the flowchart illustrated in FIG. 3.

Second Exemplary Embodiment

A second exemplary embodiment of the present invention is described with reference to FIGS. 7 through 9. An X-ray imaging control apparatus (radiographic imaging control apparatus) according to the second exemplary embodiment of the present invention is similar in arrangement to the X-ray imaging control apparatus (radiographic imaging control apparatus) according to the first exemplary embodiment illustrated in FIG. 1.

Figure 7:
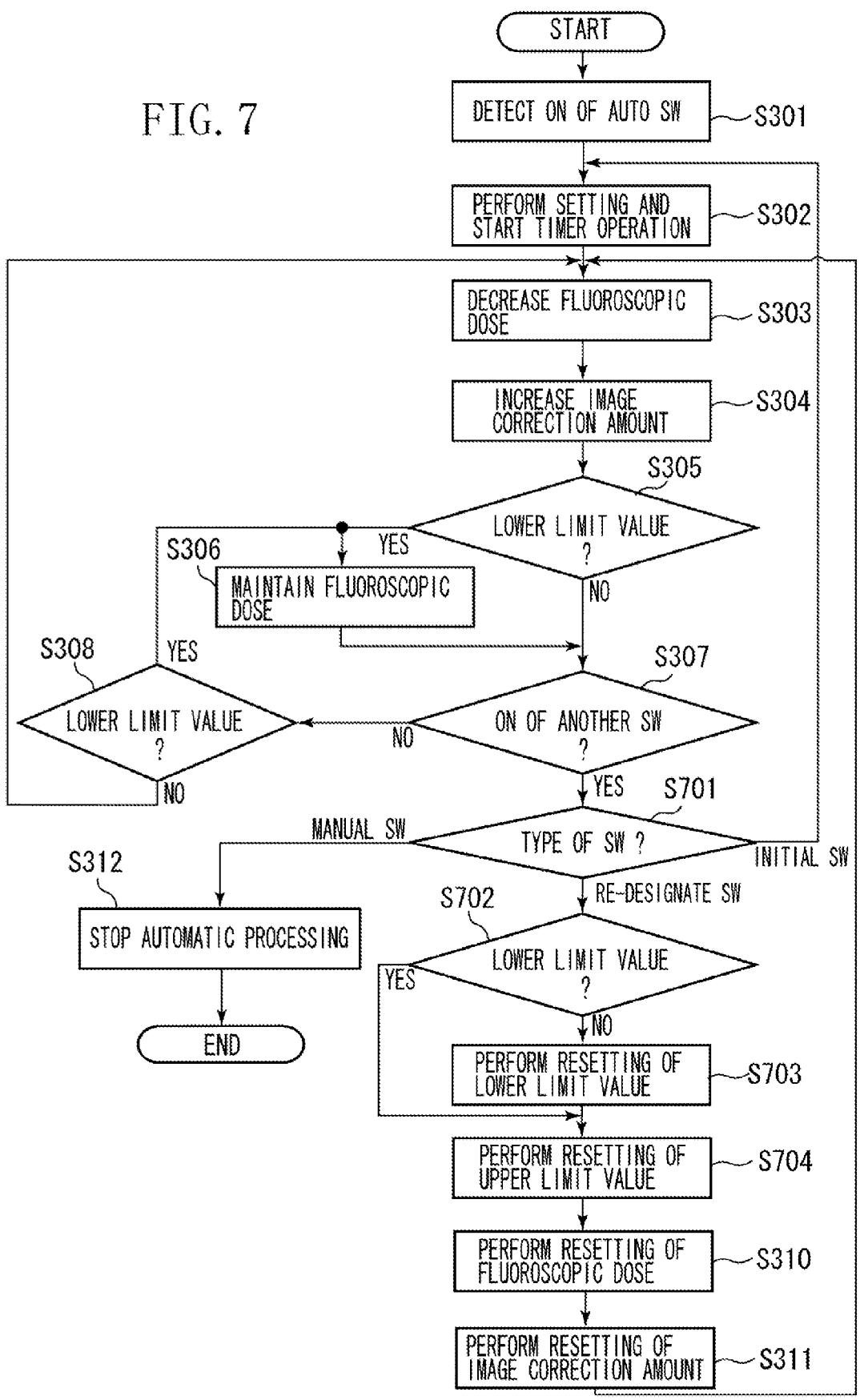
FIG. 7 is a flowchart illustrating processing performed by the X-ray image processing apparatus (radiographic image processing apparatus) according to a second exemplary embodiment of the present invention.

FIG. 7 is a flowchart illustrating example processing performed by the X-ray image processing apparatus (radiographic image processing apparatus) 102 according to the second exemplary embodiment. The flowchart illustrated in FIG. 7 includes steps similar to those illustrated in FIG. 3 (first exemplary embodiment) and denoted by the same step numbers. The processing (operations) according to this flowchart is described later.

FIGS. 8A through 8C illustrate an example relationship among fluoroscopic flux, noise amount, and image correction amount according to the second exemplary embodiment of the present invention. In FIGS. 8A through 8C, some of reference numerals are identical to those illustrated in FIGS. 5A through 5C (first exemplary embodiment).

Figure 9:
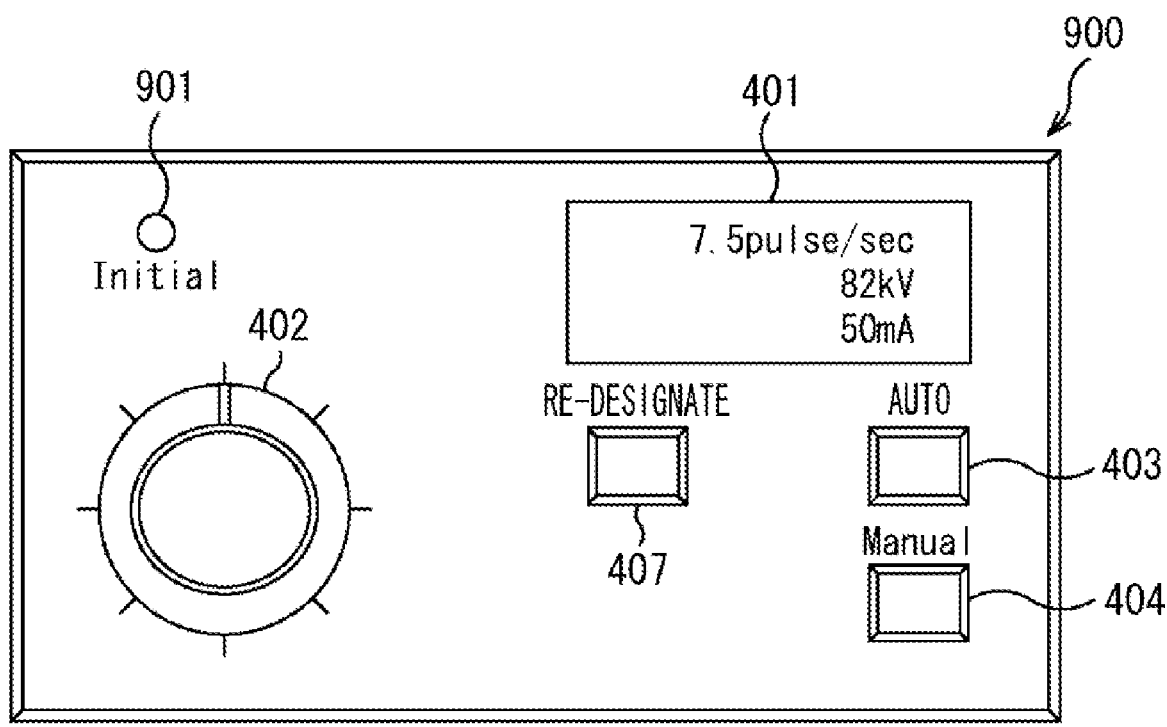
FIG. 9 illustrates an X-ray control operation panel according to the second exemplary embodiment of the present invention.

Furthermore, the second exemplary embodiment uses an X-ray control operation panel 900 illustrated in FIG. 9 which is different from the X-ray control operation panel 400 of the first exemplary embodiment illustrated in FIG. 4.

FIG. 9 illustrates an example of the X-ray control operation panel 900 according to the second exemplary embodiment. The X-ray control operation panel 900 illustrated in FIG. 9 includes components similar to those of the X-ray control operation panel 400 illustrated in FIG. 4 and denoted by the same reference numerals.

More specifically, the X-ray control operation panel 900 according to the second exemplary embodiment includes an initial switch (INITIAL SW) 901 in addition to the arrangement of the X-ray control operation panel 400 illustrated in FIG. 4. The INITIAL SW 901 is a switch enabling an operator to change an upper-limit level (maximum value) 806 and a lower-limit level (minimum value) 807 illustrated in FIG. 8A, which are once set by an operator, to the upper-limit level (maximum value) 503 and the lower-limit level (minimum value) 504 which are predetermined initial setting values.

In FIGS. 8A through 8C, time 801 represents the time when the RE-DESIGNATE SW 407 of FIG. 9 is first pressed. Furthermore, time 802 represents the time when the RE-DESIGNATE SW 407 is next pressed. Moreover, the time 803 represents time when the INITIAL SW 901 of FIG. 9 is pressed.

FIG. 8A illustrates the temporal change of a fluoroscopic flux 805 controlled by the system control unit 103 via the fluoroscopic flux control unit 115. The upper-limit level (maximum value) 806 and the lower-limit level (minimum value) 807 are an upper-limit level (maximum value) and a lower-limit level (minimum value) which an operator can arbitrarily determine by performing a resetting operation.

FIG. 8B illustrates the temporal change of a noise amount 811 involved in an analog signal of the fluoroscopic image (X-ray image) output from the image sensor 101 in contrast with the change of the fluoroscopic flux 805. As apparent from FIG. 8B, the noise amount 811 increases monotonously according to reduction of the fluoroscopic flux 805 illustrated in FIG. 8A.

FIG. 8C illustrates the temporal change of an image correction amount 821 for the image correction processing performed by the image correction unit 105 under the control of the system control unit 103 to decrease the noise amount 811 generated according to the change of the fluoroscopic flux 805.

More specifically, the operator presses the RE-DESIGNATE SW 407 at the first time 801 after the fluoroscopic flux 805 has once reached the predetermined lower-limit level (minimum value) 504 which is a predetermined initial setting value. In this case, the system control unit 103 determines that the operator permits the diagnosis being performed with the fluoroscopic flux 805 set to the predetermined lower-limit level (minimum value) 504. The system control unit 103 does not perform resetting for changing the lower-limit level (minimum value).

In this case, the operator is adaptive to the image quality of a fluoroscopic image obtained while the fluoroscopic flux 805 decreases to the lower-limit level (minimum value) 504. The system control unit 103 performs resetting for decreasing the upper-limit level (maximum value). The reset value of the upper-limit level (maximum value) 806, which is determined by an operator through the reset processing, is a value smaller than the predetermined upper-limit level (maximum value) 503 and is recorded (stored) in a predetermined area of the flash memory 118 (recording medium) under the control of the system control unit 103. The upper-limit level (maximum value) 806, i.e., the predetermined reset value, is effective until an operator presses the INITIAL SW 901 at time 803. According to this exemplary embodiment, the fluoroscopic flux 805 jumps to the upper-limit level (maximum value) 806 if the RE-DESIGNATE SW 407 is pressed.

Then, the operator presses the RE-DESIGNATE SW 407 again at the second time 802 before the fluoroscopic flux 805 reaches the predetermined lower-limit level (minimum value) 504 having been initially set. In this case, the system control unit 103 performs resetting for increasing the lower-limit level (minimum value) 504 on the assumption that the operator has pressed the RE-DESIGNATE SW 407 because the diagnosis cannot be performed with the fluoroscopic flux 805 set to the lower-limit level (minimum value) 504.

The fluoroscopic flux control unit 115 sets the new lower-limit level (minimum value) 807 corresponding to the fluoroscopic flux 805 at the time the RE-DESIGNATE SW 407 is pressed, while performing the processing for decreasing the fluoroscopic flux 805. The reset value of the lower-limit level (minimum value) 807, which is determined by an operator through the reset processing, is recorded (stored) in a predetermined area of the flash memory 118 (recording medium) under the control of the system control unit 103. The lower-limit level (minimum value) 807, i.e., the predetermined reset value, is effective until an operator presses the INITIAL SW 901 at time 803.

The system control unit 103 reads the setting value relating to the image correction amount from the flash memory 118 according to the setting value relating to the fluoroscopic flux for the fluoroscopic flux control unit 115, and sets the read setting value to the image correction unit 105.

Next, example processing (operations) performed by the X-ray image processing apparatus (radiographic image processing apparatus) 102 according to the second exemplary embodiment is described below with reference to the flowchart illustrated in FIG. 7.

In step S301, the system control unit 103 detects if an operator presses the AUTO SW 403 when the operator performs diagnosis while viewing the display device 108.

In step S302, the system control unit 103 reads initial setting values relating to the fluoroscopic flux 805 (e.g., upper-limit level (maximum value) 503, lower-limit level (minimum value) 504, and change amount) from a predetermined area of the flash memory 118, and sets the read setting values to the fluoroscopic flux control unit 115. Furthermore, the system control unit 103 reads an initial setting value relating to the image correction amount 821 from the flash memory 118, and sets the read setting values to the image correction unit 105. Furthermore, the system control unit 103 causes the timer unit 111 to start a timer operation.

In step S303, the system control unit 103 causes the fluoroscopic flux control unit 115 to decrease the fluoroscopic flux according to the basic change amount represented by the fluoroscopic flux 805 illustrated in FIG. 8A in association with the timer operation of the timer unit 111. The fluoroscopic flux control unit 115 instructs the X-ray generation apparatus 100 to gradually decrease the X-ray flux (fluoroscopic flux) from the predetermined upper-limit level (maximum value) 503 when the X-ray generation apparatus 100 irradiates the subject 202 with X-rays.

In step S304, the system control unit 103 causes the image correction unit 105 to perform image correction processing according to the basic setting amount to decrease the fluoroscopic flux. The image correction unit 105 performs image correction processing based on the image correction amount 821 which increases in a stepwise fashion as illustrated in FIG. 8C. Namely, the system control unit 103 performs a control for increasing the image correction amount relating to the image correction processing performed by the image correction unit 105 according to a change amount corresponding to the reduction in the fluoroscopic flux.

In step S305, the system control unit 103 determines whether the fluoroscopic flux 805 has reached the predetermined lower-limit level (minimum value) 504, while constantly monitoring the fluoroscopic flux 805 during the fluoroscopic flux reduction processing having been started in step S303.

If the system control unit 103 determines that the fluoroscopic flux 805 has reached the predetermined lower-limit level (minimum value) 504 (YES in step S305), the processing proceeds to step S306.

In step S306, the system control unit 103 causes the fluoroscopic flux control unit 115 to maintain the fluoroscopic flux 805 at the lower-limit level (minimum value) 504 and also causes the image correction unit 105 to maintain the image correction amount 821 at a present level.

After completing the processing of step S306, the processing proceeds to step S307. Furthermore, if the system control unit 103 determines that the fluoroscopic flux 805 has not yet reached the predetermined lower-limit level (minimum value) 504 (NO in step S305), the processing proceeds to step S307.

In step S307, the system control unit 103 determines whether an operator operates (presses) any switch other than the AUTO SW 403 on the X-ray control operation panel 900 illustrated in FIG. 9. If the system control unit 103 determines that a switch other than the AUTO SW 403 is not operated (pressed) (NO in step S307), the processing proceeds to step S308.

In step S308, the system control unit 103 determines whether the fluoroscopic flux 805 has reached the predetermined lower-limit level (minimum value) 504. If in step S308 it is determined that the fluoroscopic flux 805 has reached the predetermined lower-limit level (minimum value) 504 (YES in step S308), the processing returns to step S306. Furthermore, if the system control unit 103 determines that the fluoroscopic flux 805 has not yet reached the predetermined lower-limit level (minimum value) 504 (NO in step S308), the processing returns to step S303.

If the system control unit 103 determines that a switch other than the AUTO SW 403 is operated (pressed) (YES in step S307), the processing proceeds to step S701.

In step S701, the system control unit 103 identifies the type of the switch which the operator has operated (pressed) on the X-ray control operation panel 900. If in step S701 the system control unit 103 determines that the INITIAL SW 901 is operated (pressed) by the operator, the processing returns to step S302.

If in step S701 the system control unit 103 determines that the RE-DESIGNATE SW 407 is operated (pressed) by the operator, the processing proceeds to step S702. In step S702, the system control unit 103 determines whether the fluoroscopic flux 805 has reached the lower-limit level (minimum value) 504 which is an initial setting value.

If the system control unit 103 determines that the fluoroscopic flux 805 has not yet reached the lower-limit level (minimum value) 504 having been initially set (e.g., the timing 802 illustrated in FIG. 8) (NO in step S702), the processing proceeds to step S703. In step S703, the system control unit 103 records the lower-limit level (minimum value) 807 corresponding to the fluoroscopic flux 805 at the time the RE-DESIGNATE SW 407 is pressed into a predetermined area of the flash memory 118, while performing resetting of the lower-limit level (minimum value).

After completing the processing of step S703, the processing proceeds to step S704. Furthermore, if the system control unit 103 determines that the fluoroscopic flux 805 has reached the predetermined lower-limit level (minimum value) 504 having been initially set (e.g., the timing 801 in illustrated in FIG. 8) (YES in step S702), the processing proceeds to step S704.

In step S704, the system control unit 103 performs resetting for decreasing the upper-limit level (maximum value) 503 having been initially set to the upper-limit level (maximum value) 806. Then, the system control unit 103 records the setting value of the upper-limit level (maximum value) 806 having been reset into a predetermined area of the flash memory 118.

In step S310, the system control unit 103 causes the fluoroscopic flux control unit 115 to perform resetting for restoring the fluoroscopic flux 805 to the upper-limit level (maximum value) 806. The fluoroscopic flux control unit 115 instructs the X-ray generation apparatus 100 to restore the X-ray flux (fluoroscopic flux) to the upper-limit level (maximum value) 806 when the X-ray generation apparatus 100 irradiates the subject 202 with X-ray.

In step S311, the system control unit 103 causes the image correction unit 105 to perform processing for resetting the image correction amount 821 (FIG. 8C) to a setting value corresponding to the fluoroscopic flux 805 according to the control for restoring the fluoroscopic flux 805 to the upper-limit level (maximum value) 503. After completing the processing of step S311, the processing returns to step S303.

If in step S701 the system control unit 103 determines that the MANUAL SW 404 is operated (pressed) by the operator, the processing proceeds to step S312.

In step S312, the system control unit 103 stops automatic control processing having been performed after the operator has pressed the AUTO SW 403 and enables the operator to start a manual operation based on the processing parameters currently held. Then, the system control unit 103 terminates the processing routine according to the flowchart illustrated in FIG. 7.

Third Exemplary Embodiment

A third exemplary embodiment of the present invention is described with reference to FIGS. 10 through 12. An X-ray imaging control apparatus (radiographic imaging control apparatus) according to the third exemplary embodiment of the present invention is similar in arrangement to the X-ray imaging control apparatus (radiographic imaging control apparatus) illustrated in FIG. 1.

Figure 10:
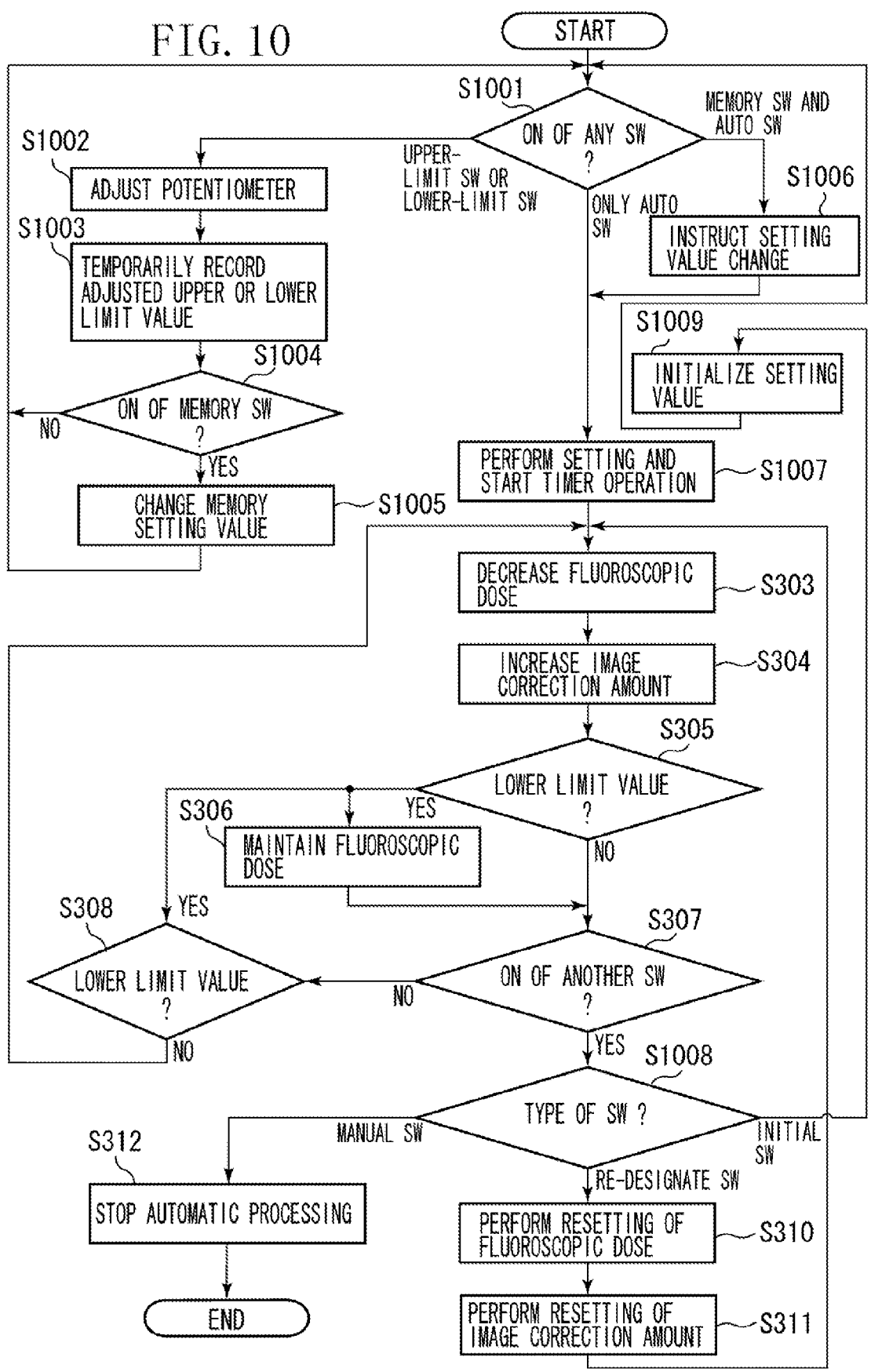
FIG. 10 is a flowchart illustrating processing performed by the X-ray image processing apparatus (radiographic image processing apparatus) according to a third exemplary embodiment of the present invention.

FIG. 10 is a flowchart illustrating processing performed by the X-ray image processing apparatus (radiographic image processing apparatus) 102 according to the third exemplary embodiment of the present invention. The flowchart illustrated in FIG. 10 includes steps similar to those illustrated in FIG. 3 (first exemplary embodiment) and denoted by the same step numbers. The processing (operations) according to this flowchart is described later.

Figure 11:
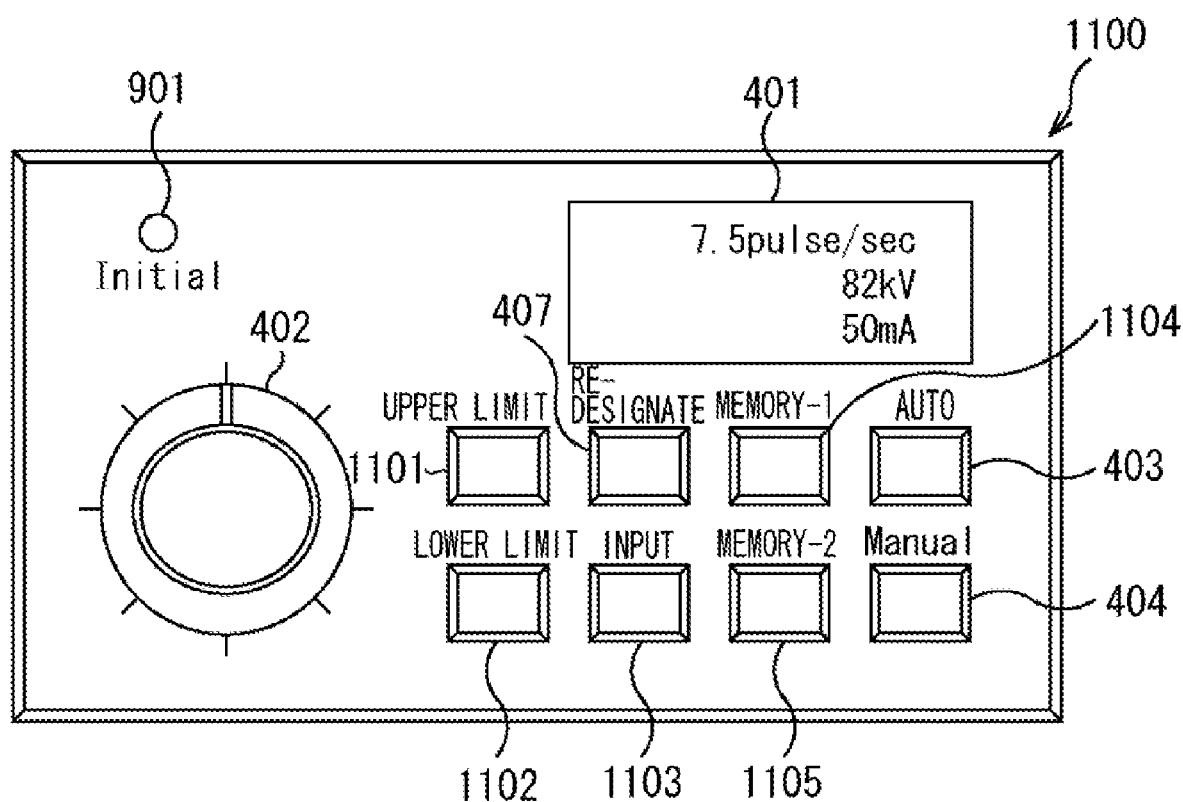
FIG. 11 illustrates an X-ray control operation panel according to the third exemplary embodiment of the present invention.

Furthermore, the third exemplary embodiment uses an X-ray control operation panel 1100 illustrated in FIG. 11 which is different from the X-ray control operation panel 400 of the first exemplary embodiment illustrated in FIG. 4 (or the X-ray control operation panel 900 of the second exemplary embodiment illustrated in FIG. 9).

FIG. 11 illustrates an example of the X-ray control operation panel 1100 according to the third exemplary embodiment. The X-ray control operation panel 1100 illustrated in FIG. 11 includes components similar to those of the X-ray control operation panel 900 illustrated in FIG. 9 and denoted by the same reference numerals. More specifically, the X-ray control operation panel 1100 according to the third exemplary embodiment includes various switches 1101 through 1105 in addition to the arrangement of the X-ray control operation panel 900 illustrated in FIG. 9.

An upper-limit switch (UPPER-LIMIT SW) 1101 is a switch enabling an operator to manually change the upper-limit level (maximum value). A lower-limit switch (LOWER-LIMIT SW) 1102 is a switch enabling an operator to manually change the lower-limit level (minimum value). An input switch (input SW) 1103 is a switch enabling an operator to set a new upper-limit level changed by manipulating the UPPER-LIMIT SW 1101 or a new lower-limit level changed by manipulating the LOWER-LIMIT SW 1102. A memory-1 switch (MEMORY-1 SW) 1104 and a memory-2 switch (MEMORY-2 SW) 1105 are switches enabling an operator to record each of the updated values of the upper-limit level and the lower-limit level.

FIGS. 12A through 12C illustrate a relationship between fluoroscopic flux, noise amount, and image correction amount according to the third exemplary embodiment of the present invention. In FIGS. 12A through 12C, timing 1201 represents time when the RE-DESIGNATE SW 407 is first pressed. Furthermore, timing 1202 represents time when the RE-DESIGNATE SW 407 is next pressed.

FIG. 12A illustrates the temporal change of a fluoroscopic flux 1205 controlled by the system control unit 103 via the fluoroscopic flux control unit 115. If an operator presses the RE-DESIGNATE SW 407, the fluoroscopic flux 1205 is restored to a predetermined upper-limit level (maximum value) 1203 as illustrated in FIG. 12A.

More specifically, the operator presses the RE-DESIGNATE SW 407 at the first time 1201 after the fluoroscopic flux 505 has once reached the predetermined lower-limit level (minimum value) 504. Then, the operator presses the RE-DESIGNATE SW 407 again at the second time 502 before the fluoroscopic flux 1205 reaches the lower-limit level (minimum value) 1204. At each time, the fluoroscopic flux 1205 is restored to the predetermined upper-limit level (maximum value) 1203 when the operator presses the RE-DESIGNATE SW 407.

The upper-limit level (maximum value) 1203 and the lower-limit level (minimum value) 1204 of the fluoroscopic flux 1205 illustrated in FIG. 12A can be determined considering a portion of the subject 202 to be imaged, or can be arbitrarily set by an operator. If the setting processing considering the portion to be imaged is completed, the system control unit 103 performs recording (storage) of the upper-limit level (maximum value) 1203 and the lower-limit level (minimum value) 1204 into a predetermined area of the flash memory 118 (i.e., recording medium) which can be managed by the system control unit 103.

Furthermore, if the setting processing based on an operator's manual operation is completed, the system control unit 103 performs recording (storage) of the set values of the upper-limit level and the lower-limit level into an area of the flash memory 118 (i.e., recording medium) which is different from the recording area for the setting values determined according to the portion of the subject 202 to be imaged.

FIG. 12B illustrates the temporal change of a noise amount 1211 involved in an analog signal of the fluoroscopic image (X-ray image) output from the image sensor 101 in association with the change of the fluoroscopic flux 1205. As is apparent from FIG. 12B, the noise amount 1211 increases monotonically according to the reduction of the fluoroscopic flux 1205 illustrated in FIG. 12A.

FIG. 12C illustrates the temporal change of an image correction amount 1221 for the image correction processing performed by the image correction unit 105 under the control of the system control unit 103 to decrease the noise amount 1211 generated according to the change of the fluoroscopic flux 1205.

As illustrated in FIG. 12C, at the time 1201 when the RE-DESIGNATE SW 407 is first pressed, the image correction unit 105 performs processing for restoring the image correction amount to the lowest level in response to the jump of the fluoroscopic flux 1205 to the upper-limit level (maximum value) 503.

Similarly, at the time 1202 when the RE-DESIGNATE SW 407 is next pressed, the image correction unit 105 performs processing for restoring the image correction amount to the lowest level in response to the jump of the fluoroscopic flux 1205 to the upper-limit level (maximum value) 1203 even if the image correction amount has an intermediate value. If an operator presses the RE-DESIGNATE SW 407, the system control unit 103 causes the image correction unit 105 to perform a control for decreasing the image correction amount in response to the jump of the fluoroscopic flux 1205 to the upper-limit level (maximum value) 1203.

The above-described sequential processing illustrated in FIGS. 12A through 12C can be realized by the system control unit 103 that controls setting values of the fluoroscopic flux control unit 115 and the image correction unit 105 according to time information of the timer unit 111 and an operator's instruction input via the operation panel 110. The flash memory 118 can store, in a predetermined area, a basic change amount applicable to the change amount of the fluoroscopic flux 1205 illustrated in FIG. 12A. Furthermore, the flash memory 118 can store, in a predetermined area, a basic correction amount applicable to the image correction amount 1221 of the image correction unit 105 corresponding to the change of the fluoroscopic flux 1205.

Next, example processing (operations) performed by the X-ray image processing apparatus (radiographic image processing apparatus) 102 according to the third exemplary embodiment is described with reference to the flowchart illustrated in FIG. 10.

An example method for recording setting values of the upper-limit level (maximum value) and the lower-limit level (minimum value) based on the MEMORY-1 SW 1104 and the MEMORY-2 SW 1105 is described below. Furthermore, an example method for setting temporary values of the upper-limit level (maximum value) and the lower-limit level (minimum value) is described below.

In step S1001, the system control unit 103 determines whether an operator has operated (pressed) any switch on the X-ray control operation panel 1100 illustrated in FIG. 11. More specifically, in step S1001, the system control unit 103 determines whether an operator has operated the UPPER-LIMIT SW 1101 or the LOWER-LIMIT SW 1102 on the X-ray control operation panel 1100 illustrated in FIG. 11. Furthermore, the system control unit 103 determines whether the AUTO SW 403 is operated. Moreover, the system control unit 103 determines whether the AUTO SW 403 is operated after the memory SW (MEMORY-1 SW 1104 or MEMORY-2 SW 1105) is operated. If any other switch is operated, the system control unit 103 maintains a standby state in step S1001.

If in step S1001 the system control unit 103 determines that the UPPER-LIMIT SW 1101 or the LOWER-LIMIT SW 1102 is operated (pressed), the processing proceeds to step S1002. In step S1002, the system control unit 103 detects an operated amount of the potentiometer 402 if an operator adjusts the upper-limit level (maximum value) or the lower-limit level (minimum value) while viewing the fluoroscopic flux value displayed on the display panel 401

In step S1003, the system control unit 103 temporarily records the upper-limit level (maximum value) or the lower-limit level (minimum value) of the fluoroscopic flux adjusted in step S1002 in response to detection of turning-on of the input SW1103. More specifically, the system control unit 103 temporarily records the upper-limit level (maximum value) or the lower-limit level (minimum value) of the fluoroscopic flux at the time the input SW1103 is pressed into a temporary recording area of the flash memory 118.

The above-described processing (operations) represents a control flow realizing the method for setting temporary upper-limit level (maximum value) and the lower-limit level (minimum value). After the input SW1103 is operated (pressed), in step S1004, the system control unit 103 determines whether an operator has operated (pressed) the memory SW (MEMORY-1 SW 1104 or MEMORY-2 SW 1105).

If the system control unit 103 determines that the memory SW (MEMORY-1 SW 1104 or MEMORY-2 SW 1105) is operated (pressed) by the operator (YES in step S1004), the processing proceeds to step S1005.

In step S1005, the system control unit 103 performs processing for transferring the setting value temporarily stored in the temporary recording area of the flash memory 118 in step S1003 into a corresponding memory area of the same flash memory 118 according to the type of the memory SW.

More specifically, if an operator operates (presses) the MEMORY-1 SW 1104, the system control unit 103 records the setting value temporarily stored in the temporary recording area of the flash memory 118 in step S1003 into a memory-1 area of the flash memory 118. Furthermore, if an operator operates (presses) the MEMORY-2 SW 1105, the system control unit 103 records the setting value temporarily stored in the temporary recording area of the flash memory 118 in step S1003 into a memory-2 area of the flash memory 118.

If the memory SW (MEMORY-1 SW 1104 or MEMORY-2 SW 1105) is not operated (pressed) by the operator (NO in step S1004), the processing returns to step S1001.

The above-described processing (operations) represents a control flow realizing the method for recording a setting value of the upper-limit level (maximum value) or the lower-limit level (minimum value) in response to detection of turning-on of the MEMORY-1 SW 1104 or the MEMORY-2 SW 1105.

The third exemplary embodiment performs automatic control processing (operations), an automatic control with temporarily set values of the upper-limit level and the lower-limit level, and an automatic control using the memory.

If in step S1001 the system control unit 103 determines that the AUTO SW 403 is operated (pressed) under the condition that all of the UPPER-LIMIT SW 1101, the LOWER-LIMIT SW 1102, and the memory SW (MEMORY-1 SW 1104 or MEMORY-2 SW 1105) are not operated (pressed), the processing proceeds to step S1007.

In step S1007, the system control unit 103 reads setting values of the upper-limit level and the lower-limit level for the fluoroscopic flux determined beforehand based on a portion to be imaged from a predetermined area of the flash memory 118. Then, the system control unit 103 sets the read setting values of the upper-limit level and the lower-limit level for the fluoroscopic flux to the fluoroscopic flux control unit 115, which correspond to the upper-limit level (maximum value) 1203 and the lower-limit level (minimum value) 1204 illustrated in FIG. 12A.

In step S1007, the system control unit 103 reads the setting value relating to the image correction amount 1221 from a predetermined area of the flash memory 118 and sets the read setting values to the image correction unit 105. Furthermore, the system control unit 103 causes the timer unit 111 to start a timer operation.

If in step S1001 the system control unit 103 determines that the UPPER-LIMIT SW 1101 or the LOWER-LIMIT SW 1102 is operated (pressed), the system control unit 103 executes the processing of steps S1002 and S1003. Then, if in step S1004 the system control unit 103 determines that the memory SW (MEMORY-1 SW 1104 or MEMORY-2 SW 1105) is not operated (pressed), the processing returns to step S1001. If in step S1001 the system control unit 103 determines that the AUTO SW 403 is operated (pressed), the processing proceeds to step S1007.

In this case, in step S1007, the system control unit 103 reads the setting value of the upper-limit level (maximum value) or the lower-limit level (minimum value) temporarily stored into the temporary recording area of the flash memory 118 in step S1003. Then, the system control unit 103 sets the setting value of the upper-limit level or the lower-limit level temporarily stored into the flash memory 118 in step S1003 to the fluoroscopic flux control unit 115, which correspond to the upper-limit level (maximum value) 1203 and the lower-limit level (minimum value) 1204 illustrated in FIG. 12A.

The system control unit 103 prioritizes the setting value of the upper-limit level or the lower-limit level temporarily stored into the flash memory 118 over the setting value of the upper-limit level or the lower-limit level determined beforehand based on a portion to be imaged. For example, the flash memory 118 can store temporary setting values of both the upper-limit level and the lower-limit level if the system control unit 103 repetitively performs the processing of step S1003.

In this case, the system control unit 103 can perform setting of the upper-limit level (maximum value) 1203 and the lower-limit level (minimum value) 1204 based on these setting values. Furthermore, in step S1007, the system control unit 103 reads the setting value relating to the image correction amount 1221 from the predetermined area of the flash memory 118 and sets the read setting value to the image correction unit 105. Furthermore, the system control unit 103 causes the timer unit 111 to start a timer operation.

Furthermore, if in step S1001 the system control unit 103 determines that the AUTO SW 403 is operated (pressed) after the memory SW (MEMORY-1 SW 1104 or MEMORY-2 SW 1105) is operated (pressed), the processing proceeds to step S1006.

In step S1006, the system control unit 103 reads the setting value of the upper-limit level (maximum value) or the lower-limit level (minimum value) which has been stored into the memory area (memory-1 area or memory-2 area) of the flash memory 118 in step S1005. In this case, if the setting value of the upper-limit level (maximum value) or the lower-limit level (minimum value) is recorded in both the memory-1 area and the memory-2 area, the system control unit 103 reads the latest setting value. Then, in step S1006, the system control unit 103 instructs setting value change based on the read setting value. Then, the processing proceeds to step S1007.

In this case, in step S1007, the system control unit 103 sets the setting value of the upper-limit level or the lower-limit level read out of the memory area of the flash memory 118 in step S1006 to the fluoroscopic flux control unit 115, which correspond to the upper-limit level (maximum value) 1203 and the lower-limit level (minimum value) 1204 illustrated in FIG. 12A.

The system control unit 103 prioritizes the setting value of the upper-limit level or the lower-limit level temporarily stored into the flash memory 118 over the setting value of the upper-limit level or the lower-limit level determined beforehand based on a portion to be imaged. Furthermore, in step S1007, the system control unit 103 reads the setting value relating to the image correction amount 1221 from the predetermined area of the flash memory 118 and sets the read setting value to the image correction unit 105. Furthermore, the system control unit 103 causes the timer unit 111 to start a timer operation.

After completing the processing of step S1007, the system control unit 103 executes the processing of steps S303 through S308 illustrated in FIG. 3.

Then, if in step S307 the system control unit 103 determines that an operator has operated (pressed) any switch other than the AUTO SW 403, such as RE-DESIGNATE SW 407, MANUAL SW 404, or INITIAL SW 901, on the X-ray control operation panel 1100, the processing proceeds to step S1008.

In step S1008, the system control unit 103 identifies the type of the switch which the operator has operated (pressed) on the X-ray control operation panel 1100. If in step S1008 the system control unit 103 determines that the RE-DESIGNATE SW 407 is operated (pressed) by the operator, the system control unit 103 executes the processing of steps S310 and S311 described with reference to FIG. 3. Then, the processing returns to step S304.

Furthermore, if in step S1008 the system control unit 103 determines that the MANUAL SW 404 is operated (pressed) by the operator, the system control unit 103 executes the processing of step S312 described with reference to FIG. 3 and terminates the processing routine according to the flowchart illustrated in FIG. 10.

Furthermore, if in step S1008 the system control unit 103 determines that the INITIAL SW 901 is operated (pressed) by the operator, the processing proceeds to step S1009. In step S1009, the system control unit 103 performs processing for initializing the setting values having been set in step S1007. Then, the processing returns to step S1001. The system control unit 103 restarts the processing of step S1001 and the following steps. According to the above-described exemplary embodiment, the processing proceeds from step S1009 to step S1001. However, according to another exemplary embodiment, the processing can proceed from step S1009 to step S1007. In this case, the setting value used in step S1007 is the setting value determined when only the AUTO SW 403 is operated (pressed).

According to the examples illustrated in FIGS. 5A through 5C, FIGS. 8A through 8C, and FIGS. 12A through 12C, the X-ray flux starts falling immediately after initiation of the X-ray imaging operation. However, the system control unit 103 can be configured to start decreasing the X-ray flux when a predetermined time has elapsed after initiation of the X-ray imaging operation.

Furthermore, software program code for realizing the functions of the above-described exemplary embodiments can be supplied to a system or an apparatus including various devices. A computer (or CPU or micro-processing unit (MPU)) in the system or the apparatus can execute the program to operate the devices to realize the functions of the above-described exemplary embodiments. Accordingly, the present invention encompasses the program code installable on a computer when the functions or processes of the exemplary embodiments can be realized by the computer.

The functional components constituting the X-ray image processing apparatus 102 illustrated in FIG. 1 which relate to each exemplary embodiment, as well as the steps of FIGS. 3, 7 and 10 which realize the X-ray image processing method, can be realized by a computer that performs various operations based on software program(s) stored in a random access memory (RAM) or a read only memory (ROM). The present invention encompasses such program(s) and a computer-readable storage medium storing the program(s).

Furthermore, the present invention encompasses supplying the program(s) to a computer with a storage (or recording) medium storing the program code. A storage medium supplying the program(s) can be any one of a floppy disk, a hard disk, an optical disk, a magneto-optical (MO) disk, a compact disk-ROM (CD-ROM), a CD-recordable (CD-R), a CD-rewritable (CD-RW), a magnetic tape, a nonvolatile memory card, a ROM, and a DVD (DVD-ROM, DVD-R).

A transmission medium of the program(s) is, for example, any communication medium available for a computer network (any one of LAN, WAN (e.g., Internet), and wireless communication network) system that can transmit a carrier signal including program information. Furthermore, the communication medium is a wired communication medium (e.g., optical fiber) or a wireless communication medium.

Furthermore, the present invention is not limited to a computer executing supplied program(s) to realize the X-ray image processing apparatus 102 according to the exemplary embodiments. Moreover, an operating system (OS) or other application software running on a computer can realize the functions of the X-ray image processing apparatus 102 according to the exemplary embodiments Additionally, the program code read out of a storage medium can be written into a memory of a function expansion board equipped in a computer or into a memory of a function expansion unit connected to the computer. In this case, based on an instruction of the program, a CPU provided on the function expansion board or the function expansion unit can execute part or the whole of the processing so that the functions of the X-ray image processing apparatus 102 according to the above-described exemplary embodiments can be realized.

The X-ray image processing apparatus 102 according to the exemplary embodiments of the present invention includes the fluoroscopic flux control unit 115 that can change the X-ray flux when the X-ray generation apparatus 100 irradiates the subject 202 with X-rays. The image correction unit 105 performs image correction processing on an X-ray image obtained when the X-ray generation apparatus 100 irradiates the subject 202 with X-rays. The system control unit 103 causes the image correction unit 105 to change an image correction amount for the image correction processing if the fluoroscopic flux control unit 115 changes the X-ray flux.

Accordingly, the X-ray image processing apparatus 102 according to the exemplary embodiments can obtain an X-ray image having an image quality sufficient for performing a diagnosis, while minimizing the X-ray flux of X-ray emitted toward the subject 202. Thus, the X-ray image processing apparatus 102 according to the exemplary embodiments can prevent the image quality of an X-ray image from deteriorating without excessively irradiating the subject 202 with X-rays.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2007-123790 filed May 8, 2007, which is hereby incorporated by reference herein in its entirety.

What is claimed is:

1. A radiographic imaging control apparatus comprising:
   an input unit configured to input a radiographic image from a sensor that detects radiant rays;
   a control unit configured to cause a radiant ray generation apparatus to decrease a flux of radiant rays from an upper-limit level to a lower-limit level as time passes when the radiant ray generation apparatus irradiates the sensor with radiant rays; and
   an image correction unit configured to increase a correction amount for image correction processing as time passes when the control unit causes the radiant ray generation apparatus to decrease the flux of radiant rays.

2. The radiographic imaging control apparatus according to claim 1, further comprising an operation unit configured to increase the flux of radiant rays emitted from the radiant ray generation apparatus,
   wherein the control unit causes the radiant ray generation apparatus to restore the flux of radiant rays to a value smaller than the upper-limit level in response to operator input.

3. The radiographic imaging control apparatus according to claim 1, wherein the control unit resets the lower-limit level to a present value of the flux of radiant rays in response to an external input.

4. A radiant ray imaging apparatus comprising:
   a radiant ray generating unit;
      a radiant ray imaging unit configured to provide an image of at least part of a subject formed by radiant rays;
   a control unit operable to cause a radiant ray generation apparatus to decrease a flux of radiant rays from an upper-limit level to a lower-limit level as time passes when the radiant ray generation apparatus irradiates the radiant ray imaging unit with radiant rays;
   an image processing unit configured to process radiant ray images;
   an image correction unit configured to increase a correction amount for image correction processing as time passes when the control unit causes the radiant ray generation apparatus to decrease the flux of radiant rays; and
   a display unit configured to display radiant ray images.

5. A method for controlling a radiographic imaging control apparatus, the method comprising
  decreasing a flux of radiant rays from an upper-limit level value to a lower-limit level as time passes when a sensor is irradiated with radiant rays;
  increasing a correction amount for image correction processing as time passes when the flux of radiant rays is decreased; and
  inputting a radiographic image from the sensor.

6. The method according to claim 5, further comprising restoring the flux of radiant rays to a value smaller than the upper-limit level in response to an external input.

7. The method according to claim 5, further comprising resetting the lower-limit level to a present value of the flux of radiant rays in response to an external input.

8. A computer-readable storage medium storing a program, the program causing a computer to control a radiographic imaging control apparatus, the program comprising:
  decreasing the flux of radiant ray from an upper-limit level to a lower-limit level as time passes when a sensor is irradiated with radiant rays;
  increasing a correction amount for image correction processing as time passes when the flux of radiant rays is decreased; and
  inputting a radiographic image from the sensor.

9. The computer-readable storage medium according to claim 8, wherein the program further comprises restoring the flux of radiant ray to a value smaller than the upper-limit level in response to an external input.

10. The computer-readable storage medium according to claim 8, wherein the program further comprises resetting the lower-limit level to a present value of the flux of radiant ray in response to an external input.

* * * * *